United States Patent [19]

Rodland et al.

[11] Patent Number: 4,908,307
[45] Date of Patent: Mar. 13, 1990

[54] HYBRIDIZATION METHOD AND PROBE FOR DETECTING NUCLEIC ACID SEQUENCES

[75] Inventors: Karin D. Rodland, 3330 NE. 138th Pl., Portland, Oreg. 97230; Peter J. Russell, Portland, Oreg.

[73] Assignee: Karin D. Rodland, Portland, Oreg.

[21] Appl. No.: 944,678

[22] Filed: Dec. 19, 1986

[51] Int. Cl.⁴ .................... C12Q 1/68; G01N 33/566; C07H 15/12; C12N 15/00
[52] U.S. Cl. ...................................... 435/6; 436/501; 536/27; 935/1; 935/7; 935/16; 935/23; 935/78; 935/79; 935/88
[58] Field of Search ..................... 435/6, 91; 436/501; 536/27; 935/1, 7, 16, 23, 78, 79, 88

[56] References Cited

U.S. PATENT DOCUMENTS

| | | | |
|---|---|---|---|
| 4,302,204 | 11/1981 | Wahl et al. | 23/230.3 |
| 4,358,535 | 11/1982 | Falkow et al. | 435/5 |
| 4,399,216 | 8/1983 | Axel et al. | 435/6 |
| 4,455,370 | 6/1984 | Bartelsman et al. | 435/6 |
| 4,521,509 | 6/1985 | Benkovic et al. | 435/6 |
| 4,599,303 | 7/1986 | Yabusaki et al. | 435/6 |
| 4,647,529 | 3/1987 | Rodland et al. | 435/6 |

OTHER PUBLICATIONS

Southern, "Detection of Specific Sequences Among DNA Fragments Separated by Gel Electrophoresis," *J. Mol. Biol.* 98: 503–517 (1975).
Noyes and Stark, "Nucleic Acid Hybridization Using DNA Covalently Coupled to Cellulose," *Cell* 5: 301–309 (1975).
Alwine, Kemp and Stark, "Method for Detection of Specific RNAs in Agarose Gels by Transfer to Diazobenzyloxymethyl–Paper and Hybridization with DNA Probes," *Proc. Natl. Acad. Sci. U.S.A.* 74: 5350–5354 (1977).
Reiser, Renart and Stark, "Transfer of Small DNA Fragments From Polyacrylamide Gels to Diazobenzyloxymethyl–Paper and Detection by Hybridization With DNA Probes," *Biochem. Biophys. Res. Comm.* 85: 1104–1112 (1978).
Bittner, Kupferer and Morris, "Electrophoretic Transfer of Proteins and Nucleic Acids from Slab Gels to Diazobenzyloxymethyl Cellulose or Nitrocellulose Sheets," *Anal. Biochem.* 102: 459–471 (1980).
Reiser and Wardale, "Immunological Detection of Specific Proteins in Total Cell Extracts by Fractionation in Gels and Transfer to Diazophenylthioether Paper," *Eur. J. Biochem.* 114: 569–575 (1981).
Green and Rittenbach, "GeneScreen Hybridization Transfer Membrane," Instruction Manual, Cat. No. NEF-972, New England Nuclear (Boston, MA, 1982).
Wahl, Stern and Stark, "Efficient Transfer of Large DNA Fragments from Agarose Gels to Diazobenzyloxymethyl–Paper and Rapid Hybridization by Using Dextran Sulfate," *Proc. Nat. Acad. Sci. U.S.A.* 76: 3683–3687 (1979).

(List continued on next page.)

Primary Examiner—Amelia Burgess Yarbrough
Assistant Examiner—Ardin Marschel
Attorney, Agent, or Firm—Klarquist, Sparkman, Campbell, Leigh & Whinston

[57] ABSTRACT

Improved hybridization probe compositions and method for detecting nucleic acids of interest are provided. A hybridization probe constructed to contain thionucleotides and a detectable label is hybridized to a nucleotide sequence of interest in the absence of nonpolar solvents, reducing agents and volume exclusion agents. The thionucleotides serve to increase the mass of bound probe molecules, thereby amplifying the signal available to detect the presence of the nucleic acid sequence of interest. Certain cations interact specifically with the thiol moiety of phosphorothioate groups of nucelic acid molecules in a manner that can be exploited to amplify probe binding or convey a detectable label. Thus, the mass of bound probe molecules can be further increased by the presence of specified multivalent cations from the transition metal group, such as $Cu^{2+}$ or $Fe^{3+}$, during the annealing step.

27 Claims, 1 Drawing Sheet

OTHER PUBLICATIONS

Rigby, Dieckmann, Rhodes and Berg, "Labeling Deoxyribonucleic Acid to High Specific Activity in Vitro by Nick Translation with DNA Polymerase I," *J. Mol. Biol.* 113: 237–251 (1977).

Vincent, Beltz and Ashton, "Preparation of DNA Labeled With High Specific Activity [$^{35}$S]–Deoxyadenosine 5'–[α–Thio] Triphosphate; the Use of $^{35}$S–Labeled Nucleic Acids as Molecular Hybridization Probes," New England Nuclear Technical Bulletin (1982).

Kunkel, Eckstein, Mildvan, Koplitz and Loeb, "Deoxynucleoside[I–thio] Triphosphates Prevent Proofreading During in vitro DNA Synthesis," *Proc. Nat. Acad. Sci. U.S.A.* 78: 6734–6737 (1981).

Putney, Benkovic and Schimmel, "A DNA Fragment with an α-Phosphorothioate Nucleotide at one end is Asymmetrically Blocked From Digestion by Exonuclease III and can be Replicated in vivo," *Proc. Nat. Acad. Sci. U.S.A.* 78: 7350–7353 (1981).

Radford, "Comparisons Using $^{35}$S– and $^{32}$P–Labeled DNA for Hybridization on Nitrocellulose Filters," *Anal. Biochem.* 134: 269–271 (1983).

New England Nuclear Technical Bulletin, "New Product News," vol. 1, No. 9, (Nov. 1982).

Strothkamp and Lippard, "Platinum Binds Selectively to Phosphorothioate Groups in Mono- and Polynucleotides: A General Method for Heavy Metal Staining of Specific Nucleotides," *Proc. Nat. Acad. Sci. U.S.A.* 73: 2536–2540 (1976).

Frey and Sammons, "Bond Order and Charge Localization in Nucleoside Phosphorothioates," *Science* 228: 541–545 (1985).

Pecoraro, Hermes and Cleland, "Stability Constants of $MG^{2+}$ and $Cd^{2+}$ Complexes of Adenine Nucleotides and Thionucleotides and Rate Constants for Formation and Dissociation of MgATP and MgADP," *Biochem.* 23: 5262–5271 (1984).

Langer, Waldrop and Ward, "Enzymatic Synthesis of Biotin–Labeled Polynucleotides: Novel Nucleic Acid Affinity Probes," *Proc. Nat. Acad. Sci. U.S.A.* 78: 6633–6637 (1981).

Singer and Ward, "Actin Gene Expression Visualized in Chicken Muscle Tissue Culture by Using in situ Hybridization with a Biotinated Nucleotide Analog," *Proc. Nat. Acad. Sci. U.S.A.* 79: 7331–7335 (1982).

Rodland and Russell, *Federation Proceedings,* Abstract No. 1148, 42(7): 1954 (1983).

Rodland and Russell, "Segregation of Heterogeneous rDNA Segments During Demagnification of a *Neurospora crassa* Strain Possessing a Double Nucleolar Organizer," *Curr. Gen.* 7: 379–384 (1983).

Rodland and Russell, Poster Presentation, "Effect of Deoxycytidine 5'–[αThio]Triphosphate–[$^{35}$S] on the Reassociation Kinetics and $S_1$ Nuclease Sensitivity of Plasmid DNA," (6/7/83).

Stellwag and Dahlberg, "Electrophoretic Transfer of DNA, RNA and Protein Onto Diazobenzyloxymethyl (DBM)—Paper," *Nucl. Acids Res.* 8: 299–317 (1980).

HYBRIDIZATION METHOD AND PROBE FOR DETECTING NUCLEIC ACID SEQUENCES

This invention was made in part with Government support, and the Government has certain rights in the invention.

This application claims priority based upon application Ser. No. 616,286, filed June 1, 1984, now pending.

BACKGROUND OF THE INVENTION

1. Field of the Invention

Recent advances in the general field of molecular biology have made it possible to detect specific genes of clinical and commercial importance. For example, the structures of various genes and gene sequences associated with specific human diseases are known, as are various techniques for detecting the presence of such genes. It is therefore possible to diagnose human disease at the genetic level.

The most common technique for detecting a particular gene sequence is hybridization. A particular nucleotide sequence or "probe" is marked with a detectable label, typically a radioactive label or chemical modification, and combined with the nucleic acid sample of interest, either in situ as part of intact cells or as isolated DNA or RNA fragments. The sample can be either free in solution or immobilized on a solid substrate. If the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred and for measuring the amount of DNA/RNA sample present. The hybridization technique is of prime importance in basic research directed at understanding the relationship between nucleotide sequences and their function, as well as in diagnostic use to detect known aberrant genes or disease agents such as viruses or bacteria.

The main limitation of present gene detecting methods is that they are not sensitive enough and therefore require a relatively large amount of sample to accurately verify the existence of a particular gene sequence. This is not surprising since the detection of a single gene in the entire genetic repertoire of a human being requires locating one part in one to ten million. In fact, most hybridization methods require at least one to ten micrograms of purified DNA, representing a substantial sample of cells, to perform a reliable analysis. This limitation is particularly significant in pre-natal diagnosis of genetic disorders where only a small cell sample can be taken or in identifying infectious agents such as viruses in small tissue samples. Consequently, there is a substantial need for gene detecting methods which will increase the sensitivity of the hybridization assay without sacrificing its specificity.

2. Description of the Prior Art

The hybridization procedure typically includes the initial steps of isolating the DNA sample of interest and purifying it chemically. The DNA sample is then cut into pieces with an appropriate restriction enzyme. The pieces are separated by size through electrophoresis in a gel, usually agarose or acrylamide. The pieces of interest are transferred to an immobilizing membrane in a manner that retains the geometry of the pieces. The membrane is then dried and prehybridized to equilibrate it for later immersion in a hybridization solution.

A probe labeled with a radioactive isotope is constructed from a nucleotide sequence complementary to the DNA sample by a conventional nick translation reaction, using a DNase and DNA polymerase, although other types of labels can be used. The probe and sample are then combined in a hybridization buffer solution and held at an appropriate temperature until annealing occurs. Thereafter, the membrane is washed free of extraneous materials, leaving the sample and bound probe molecules supported on the membrane. The signal of the bound probe molecules is typically detected and quantified by autoradiography and/or liquid scintillation counting.

Southern, *J. Mol. Biol.* 98:503 (1975) teaches the transfer of DNA fragments to strips of nitrocellulose after the fragments have been resolved by electrophoresis in agarose gels. Immobilization of DNA on diazobenzyloxymethyl cellulose is taught by Noyes and Stark, *Cell* 5:301 (1975). Alwine et al., *PNAS USA* 74:5350 (1977) teach a method for detecting specific RNA molecules that are resolved in agarose gels, transferred to diazobenzyloxymethyl paper and then hybridized with DNA probes. Similarly, Reiser et al., *Biochem. Biophys. Res. Comm.* 85:1104 (1978), teach the detection of small DNA fragments resolved in polyacrylamide gels by immobilizing the same on diazobenzyloxymethyl paper and then hybridizing them to DNA probes.

Both Bittner et al., *Anal. Biochem.* 102:459 (1980) and Stellwag and Dahlberg, *Nucl. Acid Res.* 8:299 (1980) teach the use of an electrical current to transfer DNA and RNA fragments from either agarose or acrylamide gels to diazobenzyloxymethyl paper. Similarly, electrophoretic transfer of nucleic acids to diazophenylthioether paper is taught by Reiser and Wardale, *Eur. J. Biochem.* 114:569 (1981).

A New England Nuclear (Boston, Mass.) technical bulletin entitled "Gene Screen Hybridization Transfer Membrane Instruction Manual", by D. J. Green and D. R. Rittenbach (1982), teaches a modification of two different techniques ("electrophoretic transfer" and "capillary wicking") for immobilizing DNA and RNA samples on a porous substrate, specifically nylon-base membranes.

Nucleic acid probes have heretofore been labeled separately with either tritium or radioactive phosphorus [$^{32}$P] by nick translation, Rigby et al., *J. Mol. Biol.* 113:237 (1977) or with biotinylated uridine, Narayanswami, Hutchison and Ward, *J. Cell Biol.* 95:74a (1982). Other references, besides Rigby et al., identifying radioactive labels for DNA probes include Wahl et al., U.S. Pat. No. 4,302,204 ($^{32}$P); Falkow et al., U.S. Pat. No. 4,358,535 ($^{32}$P, $^3$H, $^{14}$C); and Axel, et al., U.S. Pat. No. 4,399,216 ($^{32}$P) A New England Nuclear technical bulletin, Vincent et al., "Preparation of DNA Labeled With High Specific Activity [$^{35}$S]-Deoxyadenosine 5'-[α-Thio] Triphosphate; the Use of $^{35}$S-Labeled Nucleic Acids as Molecular Hybridization Probes" (1982), teaches that a hybridization probe labeled with [$^{35}$S]-deoxyadenosine 5' [α-thio] triphosphate is qualitatively indistinguishable from a conventional $^{32}$P labeled probe.

Wahl et al., U.S. Pat. No. 4,302,204 teach the use of ionic polymers, particularly dextran sulfate, to increase the local concentration of nucleic acids in hybridization reactions and in turn increase the signal of the DNA sample of interest. It also describes the use of a depurination step to increase the efficiency with which very large nucleic acid segments are transferred from a gel to a solid membrane.

A method of incorporating a phosphorothioate analog of deoxynucleotides, namely $^{32}S$, into DNA polymers, using known DNA polymerases (*E. coli* DNA polymerase I and *E. coli* DNA polymerase III) is described by Kunkel et al., *PNAS USA* 78:6734 (1981). This reference mentions the use of thionucleotides to induce site-specific mutations as an application of the method. Putney et al., *PNAS USA* 78:7350-7354 (1981) teach that a protective effect against enzymatic degradation occurs following the incorporation of a thionucleotide ($^{32}S$) into DNA polymers.

The use of a polyfunctional disulfide compound to cross-link protein molecules is taught by Kotani et al., U.S. Pat. No. 4,287,345.

The present invention improves prior methods of detecting DNA genes and gene sequences by amplifying the detectable signal generated by bound probe molecules, thereby providing an accurate and reliable method for detecting and quantifying particular nucleotide sequences, even in relatively small samples. Accordingly, the present invention includes as its objects the following:

(1) to increase the mass of complementary DNA bound to specific gene sequences immobilized on a membrane;
(2) to increase the signal-to-noise ratio produced in hybridization reactions involving immobilized DNA;
(3) to improve the resolution of bands visualized by autoradiography of radioisotopically-labeled DNA;
(4) to produce radioisotopic probes which will provide the same intensity of autoradiographic signal as obtained with $^{32}P$-labeled probes, but with less danger of radiation exposure to the worker due to the decreased emission energy of the probe;
(5) to improve existing protocols for hybridizations, especially filter hybridizations, with $^{35}S$-labeled probes and reduce both the direct cost of the reaction mixture and the labor cost of the procedure; and
(6) to produce a system of signal amplification which is not dependent upon the use of radioisotopes and which is compatible with a variety of probe-labeling systems.

Other objects will be apparent from the Description of a Specific Embodiments.

SUMMARY OF THE INVENTION

In accordance with the foregoing objects, the present invention comprises a hybridization probe and method for detecting nucleotide sequences. Initially, a DNA sample of interest is purified chemically and cut into pieces with a suitable restriction enzyme. The pieces are separated by size by electrophoresis in a suitable gel. The pieces of interest are then typically transferred to an immobilizing medium, such as a nitrocellulose or nylon-base membrane, that retains the geometry of the pieces. The membrane is thereafter dried and prehybridized to equilibrate it for later immersion in a hybridization solution.

A probe is constructed from a nucleotide sequence complementary to the gene sample by a nick translation reaction, using both a DNase and DNA polymerase. In this reaction, a thionucleotide containing either $^{32}S$ or $^{35}S$, is incorporated into the probe molecule. If non-radioisotopic sulfur, i.e., $^{32}S$, is incorporated into the probe molecule, the molecule must also be labeled with a radioisotope, such as $^{32}P$, $^{3}H$, $^{14}C$, $^{35}S$ or $^{125}I$, or some other detectable marker, radioactive or otherwise. The probe and sample are thereafter combined in a hybridization buffer and incubated. In such buffer, the probe and sample are combined in the absence of reducing agents, nonpolar solvents and dextran sulfate. After a specified incubation period, the membrane is removed from the buffer and washed free of extraneous materials. The presence or absence of the particular nucleotide sequence is detected by autoradiography and quantified by liquid scintillation counting.

In a second embodiment of the invention, selected cations are used in conjunction with thionucleotide-containing nucleic acid probe molecules to further increase the sensitivity of nucleic acid hybridization reactions. A target DNA sample is chemically purified and/or subjected to restriction endonuclease digestion and size fractionation by electrophoresis in agarose gels. The target DNA is then immobilized on a suitable hybridization membrane, preferably of the nylon or nitrocellulose type, which is equilibrated in a pre-hybridization buffer. Nucleic acid probes complementary to the target DNA are constructed to contain a thionucleotide and a detectable label such as a radionuclide or a detectable chemical modification. The labelled probe is then allowed to anneal with the complementary target DNA by incubation in a specified hybridization buffer. The buffer contains millimolar amounts of one or more selected cations, such as $Cu^{2+}$ or $Fe^{3+}$, and preferably lacks even small amounts of both reducing agents and chelating agents. Such buffer also preferably lacks even small amounts of EDTA. Following hybridization, probe molecules which are not specifically bound to the target DNA are removed by a washing procedure of appropriate stringency. Specifically bound probe molecules are detected by an appropriate method, depending on the nature of the detectable label.

In a modified form of the second embodiment, the thionucleotide-containing probe is constructed without the desired detectable label and then allowed to anneal with the complementary target DNA in the presence of millimolar amounts of one or more selected cations, such as $Cu^{2+}$ or $Fe^{3+}$. Following annealing, the desired detectable label(s) is(are) attached to the "probe" portion of the annealed double-stranded DNA molecule.

DESCRIPTION OF THE SPECIFIC EMBODIMENTS

Figure 1:
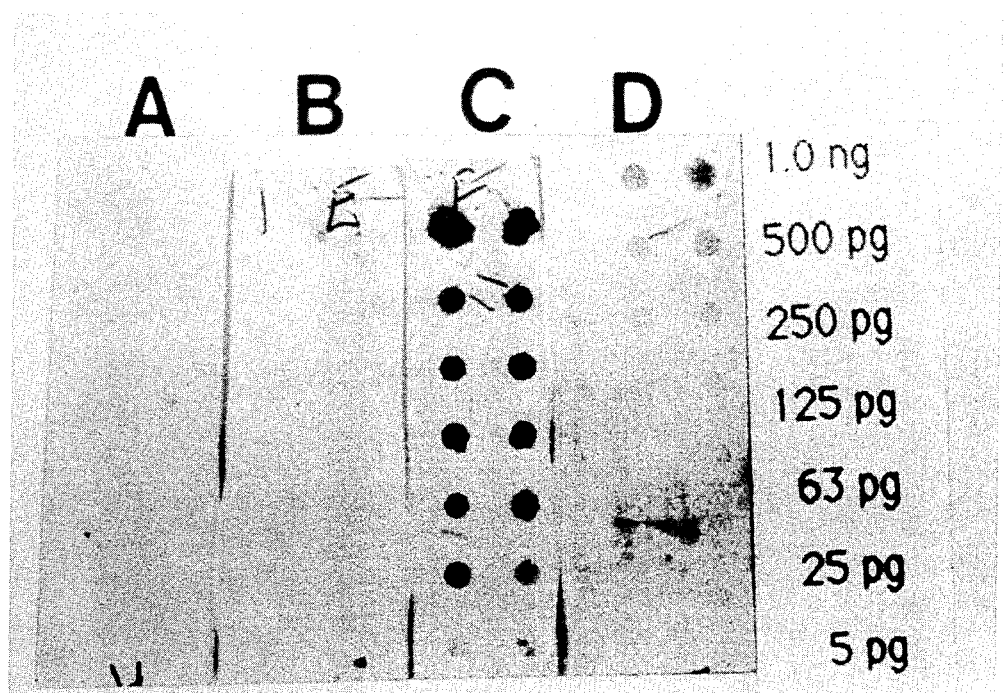

The following definitions are provided for ease in understanding the description:

thionucleotides—phosphorothioate analogs of the deoxynucleotides normally found in DNA polymers, in which a sulfur molecule has been substituted for one of the oxygen molecules in the alpha-phosphate group. A specific example is deoxycytosine-5' α-thio-triphosphate:

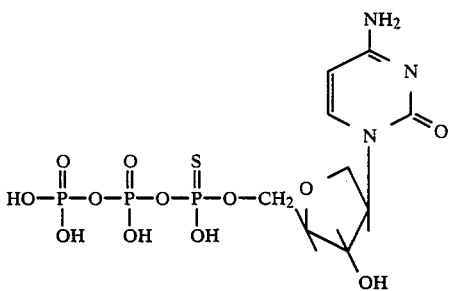

hybridization—the annealing of two complementary, single-stranded DNA molecules, particularly when the individual strands come from separate sources. The annealing is specific for complementary base pairs, and therefore reproduces the genetic code of the specific gene hybridized;

nick translation—a method for incorporating specific nucleotides into a DNA polymer by using the enzyme DNase to remove bases from the polymer (nicking) and the enzyme DNA polymerase (e.g., *E. coli* DNA polymerase I) to repair these "nicks" by incorporating nucleotide triphosphates into the DNA polymer. If the nucleotide triphosphates contain an identifiable marker, such as a radioisotopic molecule or a chemically modified base, the entire DNA polymer can be identified by detecting the marker;

hybridization membrane—a solid yet porous medium which will bind nucleic acid polymers but not free nucleotides in a non-covalent manner. The most common hybridization membranes are composed of either nitrocellulose or a surface-modified nylon;

liquid scintillation counting—a method of detecting radioactivity by detecting light emitted as a result of radioactive decay within a special chemical "fluor"; and autoradiography—a method of detecting radioactivity by exposing x-ray film to the particles of radioactive decay.

The subject invention involves four basic steps. Initially, a DNA probe molecule complementary to a nucleic acid sample of interest is constructed to have thionucleotides incorporated throughout its length and a bound detectable marker. The nucleic acid sample is preferably immobilized on a solid hybridization membrane. The sequence of these two steps is not important. The probe is then hybridized to the immobilized DNA sample under specified reaction conditions. Finally, the signal generated by probe molecules hybridized to the nucleic acid sample is detected and quantified.

Construction of the Probe Molecule

In accordance with the present invention, a preselected thionucleotide containing either $^{32}$S or $^{35}$S as the thiol group, is incorporated into DNA polymers complementary to the nucleotide sequence of interest. The resulting hybridization probe has the formula

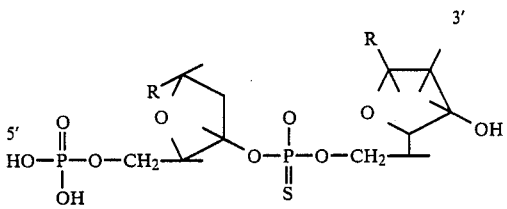

wherein R is any purine or pyrimidine base and S is either $^{32}$S or $^{35}$S.

Thionucleotide analogs of normal deoxyribonucleotides can be incorporated into nucleic acid polymers using one of several otherwise conventional techniques. One of the most common methods involves the use of the enzyme DNase I to introduce small "nicks" into one strand of a double-stranded DNA polymer. The holoenzyme form of *E. coli* DNA polymerase I can then be used to extend and repair these nicks using nucleotide triphosphates, including deoxyribonucleotide 1-O-thiotriphosphates, present in the reaction mixture. This method introduces a large number of thionucleotides randomly throughout the DNA polymer, including both strands of the double helix.

Alternatively, a variety of enzymes, including the Klenow fragment of DNA polymerase I and the T4 DNA polymerase, can be used to fill-in overhanging single-stranded regions of DNA produced by the action of restriction endonucleases. This method concentrates thionucleotides in a small region at the end of each DNA strand.

A third incorporation method, which also produces a terminal concentration of thionucleotides, involves the use of the enzyme terminal deoxynucleotidyl transferase to add a homopolymer or "tail" of deoxynucleotide 1-O-thiotriphosphates to the 3' ends of DNA polymers. With each of the foregoing methods, the double-stranded DNA probes must be denatured to single-stranded form prior to the hybridization step described below, using either heat or alkali treatment.

In yet a fourth incorporation method, labelled RNA polymers complementary to a specific DNA template can be synthesized by constructing a recombinant plasmid containing the promoter for a specific DNA-dependent RNA polymerase immediately 5' to the desired DNA sequence. The corresponding DNA-dependent RNA polymerase will synthesize a complementary RNA molecule using ribonucleotides, including ribonucleotide 1-O-thiotriphosphates, present in the reaction mixture. The resulting single-stranded probes can be used directly in a subsequent hybridization reaction, without a denaturing step.

To provide one specific illustration of how to construct a probe molecule containing an incorporated thionucleotide, the nick translation technique, as taught by Rigby et al., *J. Mol. Biol.* 113:237 (1977), will be described in greater detail. A piece of cloned DNA known to contain the coding sequence of the gene sample of interest is incubated under proper ionic conditions in a mixture containing two enzymes (DNase I and *E. coli* DNA polymerase I), preselected thionucleotides, and other necessary deoxynucleotides. The DNase enzyme removes individual nucleotides from the DNA polymers. The resulting gaps or "nicks" are then repaired by the DNA polymerase I enzyme which facilitates the linear incorporation of the thionucleotides into the DNA polymers to fill the nicks.

The thionucleotides are incorporated in accordance with the reaction conditions described in the New England Nuclear technical bulletin, Vincent et al. (1982), supra, with one modification. This technical bulletin teaches that the mixture should be incubated at 14° C. for at least 90 minutes, with a graph showing the optimum incubation period to be about 8 to 24 hours for $^{35}S$-labeled DNA. It has been determined, however, that the optimum incubation for the thiol group is at 14°–15° C. for about 5 to 6 hours, at which time about 0.1 to 1.0 pmoles of thionucleotide have been incorporated into each µg of DNA (0.03 to 0.3 ppt).

To terminate the nick translation reaction, one of several known methods may be used. One method involves separating the large thionucleotide-containing DNA polymers from the unincorporated thionucleotides by adding 2.5 volumes of ice-cold absolute ethanol and precipitating the mixture at a temperature of about −70° C. for about 20–30 minutes or overnight at about −20° C. The precipitated DNA is then collected by centrifugation in a tabletop microcentrifuge for about 10 minutes. Thereafter, the ethanol and dissolved nucleotides are discarded and the DNA polymer precipitate is re-suspended in an appropriate volume (100 µl per µg) of low ionic strength buffer consisting of a solution containing 10 mM Tris HCl, pH 7.5 (Sigma Chemical Co., St. Louis, Mo.), 10 mM $MgCl_2$ and 10 mM dithiothreitol.

When the foregoing nick translation reaction is used to radioactively label the nucleic acid probes with thionucleotides comprising, for example, deoxycytosine 5′ α[$^{35}S$] thio-triphosphate (with a specific activity of 800–1300 Ci/mmole), the probe molecules have a specific activity of 1–20×10$^6$ dpm per ug DNA. Alternatively, if non-radioactive thionucleotides, such as deoxycytosine 5′ α thio-triphosphate α [$^{32}S$] or deoxyadenosine 5′ α thio-triphosphate α-[$^{32}S$], are incorporated into the nucleic acid probes, some other detectable marker such as a radioactive label must also be incorporated. Possible radioactive labels include $^{32}P$-labeled or $^3H$-labeled deoxyadenosine triphosphate, in which case the specific activity of the probe molecules would be comparable to those obtained with $^3H$-labeled or $^{32}P$-labeled probes lacking thionucleotides. By way of example, a radioactively-labeled probe with a deoxycytosine base has the formula:

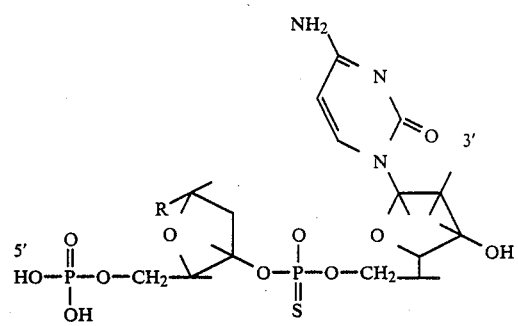

wherein R is any purine or pyrimidine base and the radioactive label is $^3H$ substituting for any H, $^{14}C$ substituting for any C, $^{32}P$ substituting for any P, $^{35}S$ substituting for the alpha thiol group in any thionucleotide or $^{125}I$ present in any iodinated modification to a purine or pyrimidine base.

The foregoing procedure can also be used with other labeling methods by which the nucleic acid probe is tagged with a non-radioactive detectable marker or in conjunction with such methods, since all nucleotide triphosphates present in the reaction mixture, including thionucleotide analogs, normal nucleotides containing a radioisotopic marker and chemically modified nucleotides (such as the biotinylated nucleotides described by Narayanswami, et al., supra), will be incorporated into the DNA sample. Thus, for example, $^{32}S$ and a biotinylated nucleotide such as biotinylated uridine can both be incorporated into the probe molecule, with the resulting formula:

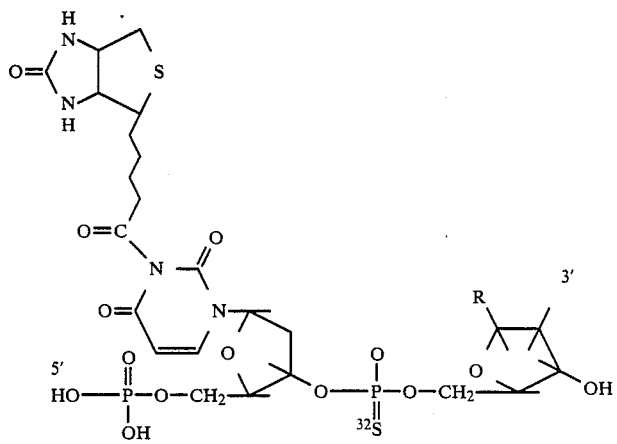

wherein R is any purine or pyrimidine base.

As a further example, the probe can be constructed with two detectable labels, a radioactive thionucleotide such as $^{35}S$ and a chemically modified nucleotide, with the resulting formula:

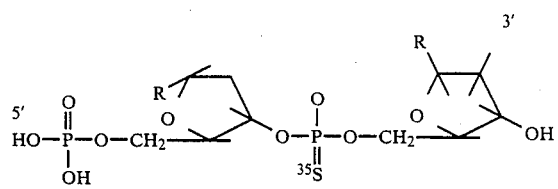

wherein R is any purine or pyrimidine base containing a detectable chemical modification and the radioactive label is $^3$H substituting for any H, $^{14}$C substituting for any C, $^{32}$P substituting for any P, $^{35}$S substituting for the alpha thiol group in any thionucleotide or $^{125}$I present in any iodinated modification to any purine or pyrimidine base.

A second example of a detectable chemical modification is a chemiluminescent modification.

Immobilization of the Nucleic Acid Sample

By way of general background, target DNA samples are generally immobilized prior to hybridization, either to preserve the geometrical relationship of size-fractionated DNA fragments or simply to facilitate detection. DNA fragments subjected to electrophoresis in agarose gels can be subjected to hybridization reactions while in the gel after appropriate denaturing and drying steps. However, it is usually advantageous to transfer the DNA fragments from the gel to an immobilizing membrane, such as nitrocellulose, diazobenzoxymethylcellulose or nylon, for convenience and stability. Transfer may be accomplished by capillary wicking or by electrophoretic transfer. Nucleic acids from bacterial colonies grown on agarose plates can also be transferred directly to membranes placed on or under the colonies. If the DNA sample is in double-stranded form, it must be denatured before hybridization can occur.

More specifically, and by way of example, the nucleic acid sample is conventionally treated to suspend the specific DNA fragments of interest in an agarose or polyacrylamide gel. The DNA fragments are treated with an alkali in a known manner to denature the double helix into two separate strands. For example, this can be accomplished by incubating the gel at room temperature for about 45–60 minutes in 0.5N NaOH, 1.5M NaCl, with gentle agitation. The gel is returned to a neutral pH by treating it with a neutralizing buffer (i.e., 1M Tris HCl, pH 6.5–7.5, 1.5M NaCl) for about 45–60 minutes at room temperature.

Thereafter, the denatured nucleic acid sample is preferably immobilized on a hybridization membrane, typically using one of two aforementioned techniques. In the case of capillary wicking, a high-salt solution is used to transfer the DNA fragments from the gel, usually an agarose gel, to the hybridization membrane. The hybridization membrane, pre-equilibrated in distilled water, is placed directly on the gel, and a sandwich is constructed. A bridge is then formed between two reservoirs of wicking buffer (such as 1.5M NaCl, 0.15M sodium citrate). A wick of chromatography paper (Whatman 3M) is laid over the bridge, extending into the reservoirs. The gel/membrane sandwich is placed on the wick, with a stack of absorbent paper pads or towels placed on top of the membrane. Capillary transfers generally require about 16–24 hours of continuous wicking for optimum results, although any transfer time between 8 and 48 hours can be used successfully.

The capillary wicking technique was initially described by Southern, *J. Mol. Biol.* 98:503 (1975) for use with nitrocellulose membranes. More recently, the technique has been used with nylon-base membranes such as "GeneScreen" and "GeneScreen Plus" introduced by New England Nuclear and other nylon membranes, including those manufactured by Pall Biodyne and Bio-Rad/AMFQ ("Zeta-Probe"). The published protocols for these nylon membranes are similar to those used with nitrocellulose membranes, although the recommended wicking buffer generally has one quarter to one half the ionic strength of the wicking buffer recommended by Southern.

The present invention works with any of the foregoing membranes, using the protocols recommended by the manufacturer, and should work with any other membranes having comparable characteristics. However, the best results are obtained with the "GeneScreen Plus" membrane, the protocol for which is described above. The foregoing procedure works with nylon membranes, regardless of whether the membrane is heated after the transfer is completed. However, with nitrocellulose membranes, the nucleic acid sample must be baked onto the membrane, preferably at 80° C. for about 2 hours, in a vacuum.

Alternatively, in the case of "electrophoretic transfer" or "electroblotting," an electric current is used as the driving force to transfer the nucleic acid fragments from either an agarose or polyacrylamide gel to the membrane. After the membrane is pre-equilibrated in distilled water or an appropriate buffer, it is placed directly on the gel, which has been treated as previously described to denature the DNA double helix, and a sandwich is constructed.

More specifically, the gel/membrane sandwich is placed in a holder especially adapted for use with an electrophoretic transfer apparatus, such as the "Trans-Blot" apparatus manufactured by Bio-Rad. The sandwich is surrounded with an appropriate buffer, such as 25 mM sodium phosphate, or a buffer containing 10 mM Tris, pH 7.8, 5 mM sodium acetate, and 0.5 mM EDTA (ethylenediaminetraacteic acid). A current of 600–800 mA is applied across the sandwich, which is positioned so that the membrane is between the gel and the anode. The DNA fragments are completely transferred to the membrane within 4–6 hours under these conditions. Overnight transfers of 14–16 hours using less current (less than 250 mA) are also feasible.

This technique was originally described by Stellwag and Dahlberg, *Nucleic Acids Res.* 8:299 (1980) and Bittner et al., *Anal. Biochem.* 102:459 (1980). Modifications of the foregoing protocol optimized for the various commercially available nylon membranes are published in the technical bulletins which accompany such membranes. The published protocols for both the "GeneScreen Plus" (New England Nuclear) and "Zeta-Probe" (Bio-Rad) membranes work well with this invention.

Yet another method of immobilizing the nucleic acid sample on a membrane, known as "dot blotting", is described more particularly in the Experimental Materials and Methods section. This technique is particularly suited for qualitative analysis in that an entire tissue sample is immobilized on the membrane without preliminary isolation of the particular nucleotide sequence of interest.

It is believed that the present invention works best with membranes having the following characteristics: nylon instead of nitrocellulose base; charge modified instead of neutral surface; and large pore size (greater than 0.45 microns). Low salt treatment of the membrane during equilibration is also favored.

Hybridization of Immobilized DNA

After the DNA sample has been transferred to the membrane, by whatever method, the gel/membrane sandwich is disassembled and any contaminating gel is gently removed from the membrane by rubbing it with the transfer buffer. The membrane is then air-dried if nylon, or baked for about 2 hours at about 80° C. in vacuo if nitrocellulose, to strengthen the binding to the membrane. The membrane is then pre-equilibrated by incubating it at about 65° C. for about 12-24 hours in a pre-hybridization buffer typically containing 0.75M NaCl, 75 mM sodium citrate or sodium phosphate, 5 mM EDTA, and 0.1 percent (w/v) sodium dodecyl sulfate (SDS).

To initiate the hybridization reaction, $1-3 \times 10^6$ cpm of radioactively-labeled probe (less than 0.5 μg) is added to a heat-resistant plastic bag containing the hybridization membrane and about 1 ml of the pre-hybridization buffer for each 50 cm$^2$ of membrane. The labeled probe is distributed throughout the bag by gentle mixing. The bag is heat-sealed, and then incubated with constant agitation for about 4-30 hours, preferably about 20 hours, at about 65° C. The hybridization reaction is carried out in the absence of nonpolar solvents such as formamide, reducing agents such as dithiothreitol and 2-mercaptoethanol, and volume exclusion agents such as dextran sulfate.

After hybridization has proceeded for the desired time interval, the radioactive probe solution is removed and treated as radioactive waste (a step obviously unnecessary if a non-radioactive labeling system is used). Non-specifically bound probe molecules are removed by a washing procedure, such as that described by Jeffreys and Flavell, *Cell* 12:429 (1977). The simplest method includes six changes of a washing solution containing 0.3M NaCl, 30 mM sodium phosphate (pH 7.4), 2 mM EDTA and 0.1 percent SDS. In each wash cycle the solution is incubated for about ten minutes at about 65° C. with constant agitation. An additional stringent wash in 15 mM NaCl, 1.5 mM sodium phosphate, 0.1 mM EDTA, 0.1 SDS for about 30 minutes at about 42° C. is preferred, but is not essential to obtain low backgrounds.

Other aqueous formulations can be used with this invention, particularly those in which sodium pyrophosphate is substituted for sodium phosphate. The addition of certain additives, such as bovine serum albumin, polyvinyl pyrrolidone, Ficoll TM (molecular weight 400), oligoribonucleotides or denatured carrier DNA is also permissible. The temperature of the hybridization reaction is not critical within a broad range determined by the base composition of the DNA sample, although temperatures between 48° C. and 70° C. are generally used.

As further explained below, increased probe binding in accordance with the present invention is not observed if the hybridization is conducted at 37° C. in 50 percent formamide. Also, the presence of either dithiothreitol or 2-mercaptoethanol, sulfhydryl containing reducing agents, or dextran sulfate in the buffer significantly reduces the binding effect.

Detection of Bound Probe Molecules

Currently, the most common technique for detecting the presence of probe molecules hybridized to the immobilized DNA is by detecting radioactive labels affixed to the probes. Such labels produce visible bands or dots when the hybridization membrane is subject to autoradiography. More specifically, the membrane is blotted partially dry and then affixed to a solid backing such as heavy paper or cardboard. Radioactive or fluorescent ink is used to define the edges and orientation of the membrane, and provide identification. The membrane is then placed in a holder with X-ray film, such as Kodak XOMAT-AR5 (TM), and allowed to expose the film for a few hours or days, depending upon the intensity of the radioactive signal. If $^{32}P$ is used as the isotope, intensifying screens (such as the DuPont Quanta II) (TM) may be used to decrease the exposure time.

In practice, autoradiography will likely be the most common detection method used with the present invention. However, bound probe molecules can also be detected and their mass measured by liquid scintillation counting of membrane squares containing immobilized DNA and bound probe molecules. The actual mass of bound probe molecules can be calculated from the observed counts and the known specific activity of the probe molecules in dpm/μg.

Alternatively, if the probe molecules are tagged with a chemical modification, such as a biotinylated nucleotide, the modification of bound probe molecules is detected in a known manner suited for the particular modification.

EXPERIMENTAL MATERIALS AND METHODS

The following examples are offered by way of illustration and not by way of limitation.

Isolation and Purification of DNA Samples

Plasmid DNA was isolated in a known manner. See, for example, Maniatis et al., *Molecular Cloning*, A Laboratory Manual, pp. 86-96 (published by Cold Spring Harbor). The specific techniques used in these experiments are described in Free, et al., *J. Bacteriol.* 137:1219-26 (1979).

Genomic DNA from *Neurospora crassa* was isolated and purified as described in Rodland and Russell, *Current Genetics* 7:379 (1983). Human genomic DNA was isolated from lymphocytes using the procedure of Gross-Ballard, *Europ. J. Biochem.* 36:32 (1973).

Preparation of DNA probes

DNA probes were labeled using the modifications of Rigby et al., *J Mol. Biol.* 113:237 (1977) described in Rodland and Russell, *Biochim Biophys Acta* 697:162 (1982) and in accordance with the protocol earlier described. The same technique was used with each of $^{32}P$, $^3H$, or $^{35}S$ as the radioactive label. Generally, a thionucleotide was incorporated into each of the experimental probes (as distinguished from the control probes). The control probes were incubated in the reaction mixture for 90 minutes, as taught by Rigby et al. However, whenever the thionucleotide deoxycytosine 5' αthio-triphosphate was incorporated into the probe, the reaction incubation was extended to 5-6 hours. The extended incubation was applied to both $^{32}S$ and $^{35}S$.

If a cold ($^{32}S$) thionucleotide was incorporated, the DNA probe was simultaneously labeled with either deoxyadenosine 5' triphosphate-[$\alpha^{32}P$] or deoxyadenosine 5' triphosphate-[2,8,5' $^3H$]. The concentration of each deoxynucleotide was kept at 15 μM, including the thionucleotides. Radioactively labeled deoxyadenosine 5' triphosphate and α-[$^{32}P$] and -[$^3H$], deoxycytosine 5' triphosphate-[$^{32}P$] and deoxycytosine 5' α thio-triphosphate used experimentally was obtained from New England Nuclear, Boston, Mass., as was the cold thionucleotide deoxycytosine 5' α thio-triphosphate α-[$^{32}S$]. Specific activities of $0.5-4.0 \times 10^7$ dpm/μg were consistently obtained, regardless of the isotope used.

Immobilization of DNA

For most of the initial experiments, the total DNA sample was immobilized on hybridization membranes using a modified "dot blot" method, without previous enzymatic digestion or size separation. By way of explanation, the general procedure for "dot-blotting" was first described by Kafatos et al., *Nucleic Acid Res.* 7:1541 (1979) for use with nitrocellulose membranes. However, the actual procedure followed was modified for use with nylon membranes as indicated below.

The DNA sample was initially denatured by a 10 minute incubation at room temperature in 0.5N NaOH. Subsequently, a tenfold excess of ice cold 0.12M sodium phosphate buffer, pH 6.5, was added and the resulting mixture immediately placed on ice to prevent re-annealing of the strands.

The nylon membranes were pre-wet in distilled water and placed on a supporting piece of chromatography paper. The paper was then placed in a "dot-blotting manifold" (BRL's Hybri-Dot (TM) or Schleicher and Schuell's Mini-Fold I (TM)). Wells of the manifold were loaded with the DNA sample. Enough DNA sample to provide 1–10 μg per well and enough of the 0.12M sodium phosphate buffer to provide a loading volume of 100 μl per well were added. An automatic pipettor (such as the FinnPipette (TM) or Gilson Pipetteman (TM)) was used to load 100 μl of this mixture into each well. The loading was accomplished by gravity filtration for one hour or less. Each well was then washed with 300 μl of the cold phosphate loading buffer, applied under gentle suction. The hybridization membrane containing the DNA samples was removed from the apparatus, air dried, and then handled in a known manner.

In two of the experiments, the DNA sample was digested with restriction endonucleases and the resulting fragments separated in agarose gels in a known manner, i.e., as taught by Southern, supra. The size-separated DNA fragments were then transferred to the hybridization membranes by either capillary transfer or electrophoretic transfer in accordance with the protocols earlier described. See also, Rodland and Russell, *Biochim Biophys Acta* 697:162 (1982); *Current Genet.* 7:379 (1983). Nylon membranes were air dried following the transfer, while nitrocellulose membranes were heated in a vacuum oven at 80° C. for 2 hours.

Hybridization of DNA Immobilized on Membranes

For hybridization purposes, all nylon and nitrocellulose membranes were treated in the same manner. The membranes were pre-hybridized by incubation at 65° C. in a buffer having 5X SSPE (0.75M NaCl, 75 mM sodium phosphate pH 6.5, 5 mM EDTA) and 0.1 percent sodium dodecyl sulfonate for 12–24 hours or, alternatively, 5X SSC (0.75M NaCl, mM sodium citrate pH 6.5) and 0.1 percent sodium dodecyl sulfate. They were pre-hybridized in heat-sealed plastic bags (i.e., Sears Seal-a-Meal (TM)), with a small volume of buffer, generally 1 ml per 50–100 $cm^2$ of membrane.

Thereafter, the probe DNA and any desired experimental additives were added directly to the unsealed bag. In these experiments, less than 1/10 volume of the additive would be added. The probe volumes were 30–75 μl, containing $1-3 \times 10^6$ cpm (100–500 μg) DNA. The probe solution was gently mixed with the pre-hybridization solution. All air bubbles were expelled, and the bag was re-sealed. No measureable quantities of any nonpolar solvents such as formamide, reducing agents such as dithiothreitol and 2-mercaptoethanol, or dextran sulfate were present in the solution, except where added to test the effect of same. The hybridization mixture was incubated for 4–30 hours, usually about 20 hours, at 65° C. with constant agitation. Nonspecifically bound probe molecules were removed by washing the membranes according to the procedure described by Jeffreys and Flavell, *Cell* 12:429 (1977). The protocol just outlined follows the hybridization protocol earlier described.

Detection and Quantification of Bound Probe Molecules

After the hybridization and washing steps, the membranes were used to expose X-ray film according to standard autoradiographic procedures to qualitatively measure the relative binding of the experimental and control probes. See, for example, Maniatis et al. manual, supra. The actual amount of probe bound was determined by liquid scintillation counting of membrane squares containing 3 or 4 "dots" of DNA, which had been treated in identical fashion. These squares were dried, placed in scintillation vials, and submerged with scintillation cocktail (i.e., Aquasol (TM) by New England Nuclear), to render the membranes translucent. Quenching was determined not to be a significant variable. A known sample of DNA probe solution was spotted onto a membrane and counted under the same conditions to determine the specific activity of the DNA probe. The mass of DNA probe bound to the membranes was then calculated from the observed cpm, quench data, and calculated specific activity of the probe in a known manner.

TABLE I

| | Relative Hybridization of DNA Probes Constructed With and Without Thionucleotides | | | | |
|---|---|---|---|---|---|
| Immobilized DNA | Experimental Probe | Ng of Bound Experimental Probe Containing Thionucleotides | Control Probe | Ng of Bound Control Probe | Binding Ratio $DNA\alpha^S/DNA$ |
| pKD002 | pKD002α[$^{35}$S] | 24.2 ± 1.55 | pKD002-[$^{32}$P] | 0.198 ± 0.002 | 120 |
| pKD002 | pKD002α[$^{35}$S] | 29.42 ± 0.21 | pKD002-[$^{32}$P] | 0.70 ± 0.15 | 42 |
| pKD002 | pKD002α[$^{35}$S] | 25.2 ± 8.9 | pKD002-[$^{32}$P] | 1.63 ± 0.66 | 15 |
| pKD003 | pKD003α[$^{35}$S] | 16.07 ± 0.31 | pKD003-[$^{32}$P] | 0.399 ± 0.18 | 40 |
| pKD003 | pKD003α[$^{35}$S] | 52.99 ± 3.12 | pKD003-[$^{32}$P] | 1.176 ± 0.234 | 45 |

EXAMPLE 1

Comparison of $^{32}$P-labeled and $^{35}$S-labeled DNA probes

Table I shows the results of several separate experiments in which probe molecule pairs, one constructed to contain deoxycytosine 5' triphosphate α-[$^{32}$P] and the other to contain deoxycytosine 5' α thiotriphosphate-[α$^{35}$S], were compared directly. In these experiments, 0.5 to 1.0 μg of DNA from the recombinant plasmid pKD002 (containing genes for rRNA from *Neurospora crassa* inserted in the plasmid pBR322) was immobilized on a "GeneScreen" membrane by dot-blotting. The membranes were hybridized in 5X SSPE, 0.1 percent SDS, at 65° C. for 24 hours. The bound DNA was measured by liquid scintillation counting. In these experiments, the mass of $^{35}$S-labeled probe bound exceeded that of the $^{32}$P-labeled probe by a factor of 15 to 120.

bilized DNA, and therefore the detectable signal, is particularly significant if the effect can be used to increase the sensitivity for detecting single copy genes in human DNA. In two experiments, shown in Table II, Part B, human genomic DNA was immobilized by dot-blotting (1 μg per dot), and probed with labeled DNA from the plasmid pJW103, which contains coding sequences for the human gamma globin gene. See Wilson et al., *Nucleic Acids Research* 5:563–81 (1978). The gamma globin gene of both the experimental and control probes was labeled with $^{32}$P as deoxyadenosine 5' triphosphate[$^{32}$P]. The control probes further incorporated deoxycytosine 5' triphosphate while the experi-

TABLE II

Relative Hybridization of DNA Probes Constructed With and Without Thionucleotides

| Immobilized DNA | Experimental Probe | Ng of Bound Experimental Probe Containing Thionucleotides | Control Probe | Ng of Bound Control Probe | Binding Ratio DNAα$^S$/DNA |
|---|---|---|---|---|---|
| Part A | | | | | |
| pKD003 | pKD003α$^{32}$S-[$^{32}$P] | 8.76 ± 0.43 | pKD003-[$^{32}$P] | 4.71 ± 0.93 | 1.86 |
| pKD003 | pKD003α$^{32}$S-[$^{32}$P] | 9.34 ± 1.36 | pKD003-[$^{32}$P] | 5.00 ± 0.22 | 1.87 |
| pKD003 | pKD003α$^{32}$S-[$^{32}$P] | 11.20 ± 0.55 | pKD003-[$^{32}$P] | 4.55 ± 0.15 | 2.46 |
| pKD003 | pKD003α$^{32}$S-[$^3$H] | 5.15 ± 0.10 | pKD003-[$^3$H] | 2.59 ± 0.11 | 1.99 |
| pKD003 | pKD003α$^{32}$S-[$^3$H] | 0.635 ± 0.114 | pKD003-[$^3$H] | 0.127 ± 0.049 | 5.0 |
| Part B | | | | | |
| human genomic DNA | pJW103α$^{32}$S-[$^{32}$P]human β-globin | 0.16 ± 0.020 | pJW103-[$^{32}$P]human β-globin | 0.04 ± 0.004 | 4.0 |
| human genomic DNA | pJW103α$^{32}$S-[$^{32}$P]human β-globin | 0.17 ± 0.012 | pJW103-[$^{32}$P]human β-globin | 0.02 ± 0.004 | 8.5 |

EXAMPLE 2

Effect of Cold Thionucleotides on Probe Binding

Another set of experiments, summarized in Table II, Part A, were conducted using the same protocol as Example 1, except that the non-radioactive thionucleotide deoxycytosine 5' α thiotriphosphate α-[$^{32}$S] was incorporated into DNA probes labeled with either $^{32}$P (deoxyadenosine 5' triphosphate-[α$^{32}$P]) or $^3$H (deoxyadenosine 5' triphosphate-[2,8,5' $^3$H]) As with Example 1, such probes were compared to conventional control probes lacking thionucleotides. In these experiments, the incorporation of cold thionucleotides increased the mass of probe bound by a factor of about 2 to 5. These experiments neutralized any difference in radiolysis between $^{35}$S and $^{32}$P (due to the higher decay energy of the latter) as the sole cause of the increased binding phenomena in Example 1. This series of experiments demonstrated that the increased binding effect is specific to the inclusion of a thionucleotide, and independent of the radioisotope used to label the DNA molecule.

EXAMPLE 3

Amplification of Probe Binding When Genomic DNA is Used

The observation that a probe containing thionucleotides increases the amount of probe hybridized to immomental probes incorporated deoxycytosine 5' α thiotriphosphate [α$^{32}$S] (the non-radioactive isotope of sulfur). In the absence of thionucleotides, a weighted average of 0.03±0.004 ng of pJW103 was bound, compared to a weighted average of 0.165±0.016 ng of pJW103 containing the thionucleotide. This represents an amplification factor of 5.5.

In a similar experiment, 4 μg per dot of genomic *Neurospora crassa* DNA was immobilized by dot-blotting and probed with recombinant plasmid pKD003, which contains part of the gene coding for rRNA in *Neurospora crassa*, inserted into the bacterial plasmid pBR322. Both "GeneScreen" and "GeneScreen Plus" membranes were used to immobilize the DNA. These membranes were then hybridized as previously described, and the mass of probe bound measured. These calculations showed that 2.12±0.08 ng of thionucleotide-containing probe pKD003 α[$^{35}$S] had bound to the DNA immobilized on GeneScreen, compared to 0.024±0.002 ng of control probe pKD003-[$^{32}$P], for a ratio of 88 to 1. A similar effect was observed on GeneScreen Plus: 8.90±0.78 ng of thionucleotide containing probe (pKD003 α[$^{35}$S]) bound compared to 0.069±0.004 ng of control probe (pKD003-[$^{32}$P]), for a ratio of 129 to 1.

TABLE III

Effect of Different Membranes on Relative Hybridization of Lambda DNA Probes Constructed With and Without Thionucleotides

| Membrane | Experimental Probe | Ng of Bound Experimental Probe Containing Thionucleotides | Control Probe | Ng of Bound Control Probe | Binding Ratio DNAα$^S$/DNA |
|---|---|---|---|---|---|
| GeneScreen (TM) | Hind III cut | 12.36 | Hind III cut λ-[$^{32}$P] | 0.68 | 18 |

TABLE III-continued

Effect of Different Membranes on Relative Hybridization of Lambda DNA Probes Constructed With and Without Thionucleotides

| Membrane | Experimental Probe | Ng of Bound Experimental Probe Containing Thionucleotides | Control Probe | Ng of Bound Control Probe | Binding Ratio DNAα$^S$/DNA |
|---|---|---|---|---|---|
| GeneScreen Plus (TM) | λα[$^{35}$S]-[$^{32}$P] Hind III cut | 33.49 | Hind III cut λ-[$^{32}$P] | 1.94 | 17 |
| Zfta-Probe (TM) | λα[$^{35}$S]-[$^{32}$P] Hind III cut | 55.87 | Hind III cut λ-[$^{32}$P] | 2.22 | 25 |
| Pall-Biodyne (TM) | λα[$^{35}$S]-[$^{32}$P] Hind III cut | 9.15 | Hind III cut λ-[$^{32}$P] | 0.74 | 12 |
| Nitrocellulose | λα[$^{35}$S]-[$^{32}$P] Hind III cut | 0.86 | Hind III cut λ-[$^{32}$P] | 0.32 | 2.7 |

EXAMPLE 4

Comparison of Hybridization Membranes

In order to determine the generality of the observed amplification of probe binding, various commercially available hybridization membranes were tested. Bacteriophage lambda DNA previously digested with the restriction enzyme HindIII (obtained from Bethesda Research Laboratories, Gaithersburg, Md.) was fractionated by electrophoresis on agarose gels and transferred to various membranes by capillary wicking. Five identical lanes were used, with 3 μg of DNA in each lane, and each lane was covered with a different membrane strip, namely "GeneScreen" (nylon), "GeneScreen Plus" (nylon), both from New England Nuclear, "Zeta-Probe" (nylon) from BioRad, Richmond, Calif., Membrane A (nylon) from Pall Biodyne and nitrocellulose (Bethesda Research Laboratories, Gaithersburg, Md.). These membranes were treated as described in the "Materials and Methods" section and then hybridized with identical HindIII digested lambda DNA which incorporated either deoxycytosine 5' triphosphate-[$^{32}$P] alone, or deoxycytosine 5' triphosphate-[$^{32}$P] plus deoxyadenosine 5' α thio-triphosphate α-[$^{35}$S]. Hybridization was conducted as before, with the mass of bound lambda DNA being calculated from the observed cpm in the high energy $^{32}$P channel (the $^{35}$S emissions are less energetic and do not contribute at all to counts measured at this energy level). Table III shows the results of this experiment. In all the membranes tested, incorporation of thionucleotides increased the mass of lambda DNA bound in comparison to the conventional control probe. However, the effect is far more striking for nylon than nitrocellulose membranes.

TABLE IV

Effect of Reducing Agent on Increased Binding

| Experimental Probe | Reducing Agent | Ng of Bound Experimental Probe Hybridized in Absence of Reducing Agent | Ng of Bound Experimental Probe Hybridized in Buffer Containing Reducing Agent | Control Probe | Ng of Bound Control Probe Hybridized in Absence of Reducing Agent | Ratio of Experimental Probe Binding Plus/Minus Reducing Agent |
|---|---|---|---|---|---|---|
| pKD003α[$^{35}$S] | dithiothreitol (10 mM) | 6.95 ± 0.88 | 5.03 ± 0.88 | — | — | 0.72 |
| pKD003α[$^{35}$S] | dithiothreitol (10 mM) | 0.367 ± 0.104 | 0.147 ± 0.010 | — | — | 0.40 |
| pKD003α[$^{35}$S] | dithiothreitol (10 mM) | 0.96 ± 0.213 | 0.344 ± 0.036 | — | — | 0.36 |
| pKD003α[$^{35}$S] | dithiothreitol (10 mM) | 0.57 ± 0.06 | 0.36 ± 0.64 | — | — | 0.63 |
| pKD003α$^{32}$S-[$^{32}$P] | dithiothreitol (10 mM) | 8.76 ± 0.86 | 6.89 ± 0.98 | pKD003-[$^{32}$P] | 4.71 ± 1.86 | 0.79 |
| pKD003α$^{32}$S-[$^3$H] | dithiothreitol (10 mM) | 1.010 ± 0.114 | 0.523 ± 0.014 | pKD003-[$^3$H] | 0.668 ± 0.42 | 0.52 |
| pKD003α$^{32}$S-[$^{32}$P] | dithiothreitol (10 mM) | 9.34 ± 2.72 | 4.43 ± 1.74 | pKD003-[$^3$H] | 5.00 ± 0.44 | 0.47 |
| pKD003α[$^{35}$S] | dithiothreitol (10 mM) | 3.13 ± 0.28 | 1.94 ± 0.90 | — | — | 0.62 |
| pKD003α$^{32}$S-[$^{32}$P] | dithiothreitol (10 mM) | 11.20 ± 1.10 | 7.61 ± 0.60 | pKD003-[$^{32}$P] | 4.55 ± 0.30 | 0.68 |
| pMF2α$^{32}$S-[$^{32}$P] | 1 2-mercaptoethanol | 62.6 ± 8.4 | 54.8 ± 4.2 | pMF2-[$^{32}$P] | 19.1 ± 2.7 | 0.88 |

EXAMPLE 5

Effect of Reducing Agents

Experiments were performed in which a reducing agent (specifically either dithiothreitol or 2-mercaptoethanol) was added to the hybridization buffer. In all other respects the protocol followed was identical to that described in Examples 1 and 2. The results of these experiments are summarized in Table IV. The presence of either dithiothreitol or 2-mercaptoethanol in the hybridization buffer reduced the amount of bound probe. It has been observed that the amplification effect can be completely eliminated at very high concentrations of reducing agent.

EXAMPLE 6

Effect of Formamide

The hybridization protocol described in Examples 1 and 2 is one of at least two commonly used procedures for nucleic acid hybridization reactions. In an alternative procedure, formamide (up to 50 percent by volume) is added to the hybridization buffer to lower the melting temperature of the DNA helix, thereby allowing the re-annealing process to occur at a lower incubation temperature.

The addition of formamide (50 percent by volume) to the hybridization buffer described in Example 1 eliminates the amplification effect otherwise present when cold thionucleotides are incorporated into the probe molecule. In one experiment, the amount of probe DNA bound was compared for probes incorporating either $^{32}$P-deoxyadenosine alone or $^{32}$P-deoxycytosine plus deoxycytosine α-thio-triphosphate [$^{32}$S], with and without 50 percent formamide in the hybridization buffer. In the absence of formamide, about twice as much experimental probe (containing $^{32}$S) as control probe (24 ng vs 12 ng) bound. When formamide was present in the buffer, the amounts of bound probe were nearly identical, 14.3 ng of experimental probe as compared to 13.6 ng of control probe.

THEORETICAL BASIS OF THE INVENTION

This section attempts to provide a few theoretical bases for the increased binding phenomenon associated with the invention. While the precise chemical mechanism which causes the observed increase in probe binding is not yet thoroughly understood, enough data has been accumulated to permit generalizations about those factors which might contribute to the phenomenon.

It is clear from the combined data of Tables I and II that the inclusion of thionucleotides into DNA probe molecules consistently increases the amount of probe subsequently hybridized to immobilized DNA. The increased binding is specific for complementary sequences, and is observed with the incorporation of either radioactive or stable isotopes of sulfur into the probe.

Looking at Table I alone, it might be theorized that the increased binding phenomenon is caused by a radioisotopic effect. Since $^{32}$P has a higher emission energy than does $^{35}$S, disintegration of $^{32}$P during radioactive decay is more likely to produce significant radiolytic degradation of the DNA polymer than disintegration of $^{35}$S. A comparison of the amplification ratios obtained when DNA is labeled with $^{35}$S versus the non-radioactive isotope $^{32}$S shows that decreased radiolysis does contribute substantially to increased probe binding. However, the incorporation of non-radioactive thionucleotides still produces a significant increase in the amount of probe hybridized (Table II), and therefore decreased radiolysis alone is an insufficient explanation.

Two possible explanations for the increased binding phenomenon are supported by the data presented. One possible explanation is that the thiol groups participate in coordination complexes in which dative bonds form between thiol groups and particularly multivalent cations. Given the charge distribution on the phosphothiodiester bond in the DNA polymer, it would be theoretically possible for such coordination complexes to form between individual DNA polymers containing thionucleotides. If one member of the linked pair of thionucleotides formed Watson-Crick base pairs with the complementary strand of immobilized DNA, the additional strand(s) linked by coordination complexes would contribute to the mass of bound probe, and to the hybridization signal. This hypothesis is supported by the observation that the addition to the hybridization buffer of dithiothreitol (Cleland's reagent), a compound known to reduce the thiol group in other sulfhydryl-containing molecules, decreases or negates altogether the increased binding phenomenon. It is also supported by the negative effect which 2-mercaptoethanol has on the phenomenon.

The second explanation relates to the degree to which the membrane-immobilized nucleic acid samples are accessible to the DNA probe molecules. The "accessibility" factor has a significant effect on the amount of probe binding which occurs. The probe molecules must come into close proximity with the immobilized DNA molecule before the requisite hydrogen bonds can form. Various physical characteristics of the hybridization membrane, such as but not limited to pore size, surface charge, and hydrophobicity, are known to affect the binding of macromolecules to the membranes. Since the incorporation of thionucleotides into the probe molecule changes several physical characteristics of the molecule (e.g. decreasing the electronegativity and charge density of the molecule), it is possible that these physical changes may increase the ability of the probe molecule to penetrate the membrane and interact with the immobilized DNA molecule. However, it is not clear how the inclusion of thionucleotides would affect this process, since the precise physical nature of DNA binding to nitrocellulose and/or nylon membranes is poorly understood. In any event, the data consistently shows the existence of such effect. For example, the magnitude of the observed amplification appears to be membrane-dependent, with nylon membranes seemingly interacting synergistically with the thionucleotides to maximize the increase in probe binding.

Furthermore, the addition of formamide has a negative effect on the observed amplification, eliminating it altogether at high concentrations. Formamide is a less polar solvent than water, and reduces the melting temperature of the DNA duplex, facilitating the re-annealing process. The non-polar nature of formamide may interfere with the interactions between the thionucleotides and the immobilizing membrane to decrease binding.

Dextran sulfate is also excluded from the hybridization buffer because it negatively affects the increased binding phenomenon. The mechanism of this effect is unknown. Dextran sulfate contains a sulfate group which could be reacting with the thiol group of the thionucleotide, thereby interfering with the chemical reaction or interaction responsible for the increased binding.

These are only the most likely explanations of the phenomenon, based on currently available data. The role of other factors or mechanisms in this process may become evident as more basic research is done on the chemical mechanisms of membrane hybridization reactions.

SECOND EMBODIMENT

In accordance with a second embodiment of the present invention, certain cations interact specifically with the thiol moiety of phosphorothioate groups of nucleic acid molecules in a manner that can be exploited to amplify probe binding or convey a detectable label. The thionucleotide-containing probe molecule is constructed and the target DNA denatured and immobilized in the manner earlier described. Whenever possible, racemically pure Sp thionucleotides are much preferred as the presence of the Rp diastereomer significantly inhibits the activity of the DNA polymerases used. The hybridization reaction is also carried out in the manner earlier described, except where noted differently below.

The membrane containing the immobilized DNA is pre-equilibrated to the hybridization conditions by incubating it in a hybridization buffer which lacks the labelled probe molecules. The incubation is conducted at the temperature of the hybridization reaction for a minimum of 1 hour to overnight. The hybridization buffer used with thionucleotide probes preferably contains 0.75M NaCl, 75 mM sodium citrate (or sodium phosphate) at a pH between 6.5 and 7.5, 0.1–1 percent sodium dodecyl sulfate (SDS), and 5–20 mM $Cu^{2+}$, $Fe^{3+}$ or a functionally similar cation. While higher levels of SDS (0.5–1 percent) in the buffer reduce non-specific background binding, they also reduce the intensity of the hybridization signal and can reduce the magnitude of the increased binding effect. The hybridization buffer preferably does not contain even small concentrations of reducing agents (e.g. dithiothreitol) or chelating agents (e.g. ethylenediaminetetraacetic acid [EDTA]), although increased binding can be observed with, for example, a buffer containing 1 mM EDTA. Also, volume exclusion agents such as dextran sulfate and nonpolar solvents preferably are excluded from the buffer. Hybridization is conducted at 65° C. with constant shaking for 4–24 hours. After hybridization is completed, non-specifically bound probe molecules are removed by washing the membrane in solutions of decreasing salt concentration (initially 0.3M NaCl 30 mM Na citrate followed by 15 mM NaCl 1.5 mM Na citrate, both with 0.1 percent SDS). The temperature of the post-hybridization wash can be varied as necessary to accommodate probe-target hybrids of varying homology. A final wash in 15 mM NaCl 1.5 mM Na citrate without any SDS can be helpful in reducing background noise.

Bound probe molecules are detected in the manner earlier described, which depends upon the particular label employed. Thus, radioactively-labelled probes can be detected by autoradiography, by use of a scanning scintillator, or by liquid scintillation counting. Non-radioactive labels involve a chemical modification which is detected in an appropriate conventional manner such as by florescence, binding of antibodies or other specific interactions (i.e., biotin-avidin binding). Also, enzymes catalyzing specific dye reactions can be conjugated to antibodies, biotin or avidin to produce a visible colorimetric reaction in the presence of the appropriate dyes. Some of the cations used to further enhance the amplification effect, notably $Cu^{2+}$ and $Fe^{3+}$, can interfere with the redox reactions (such as the horseradish peroxidase reaction) used to visualize some dyes.

In a modified form of the second embodiment, a thionucleotide-containing probe molecule is constructed without the desired detectable label and then allowed to anneal with the complementary target DNA in the presence of millimolar amounts of one or more selected cations identified above. Following annealing, the desired detectable label(s) is(are) attached to the probe portion of the annealed double-stranded DNA molecule.

The following examples are offered by way of illustration and not by way of limitation.

EXAMPLE 7

Effect of $Cu^{2+}$ on Hybridization Efficiency of Non-Radiometric Probes

Bacteriophage lambda DNA was obtained from a commercial source (Bethesda Research Labs, Gaithersburg, Md.) at a concentration of 0.667 μg/μl. The double-stranded DNA was denatured in 0.5N NaOH for 10 minutes at room temperatures, then placed on ice and neutralized by dilution in a neutralizing buffer (1.5M NaCl, 0.15M Na citrate, pH 6.5). Dilutions of denatured DNA were applied to GeneScreen Plus (TM) nylon membranes (NEN Research Products) using a Hybri-Dot (TM) manifold (Bethesda Research Labs) in a series of decreasing concentrations from 1 ng/dot to 5 pg/dot. One row contained 1 ng/dot herring sperm DNA as a control for non-specific binding of the probes to non-homologous DNA. The membranes were dried at 80° C. for 1–2 hours. The membrane was divided into four strips, each containing two columns with eight rows of DNA. The strips were pre-hybridized separately in 10 ml of 0.75M NaCl, 75 mM Na citrate, 1 percent SDS for 8 hours at 65° C. In this example, the immobilized single-stranded bacteriophage lambda DNA was used to test the effect of $Cu^{2+}$ on the hybridization efficiency of non-radiometric probes in the manner described below.

Probe DNA molecules having incorporated thionucleotides were constructed by nick translation of bacteriophage lambda DNA in the presence of deoxycytidine-1-O-[$^{32}$S]-thiotriphosphate using the method of Rigby et al. (1977; *J. Mol. Biol.* 113:237). Control probes were subjected to the same nick translation reaction in the absence of thionucleotides. Unincorporated nucleotide triphosphates were removed from the nick-translated probes by precipitation in cold ethanol or by chromatography on NENSORB (TM) columns (NEN Research Products, Boston, Mass.). The DNase treatment associated with nick translation provided an appropriate DNA substrate for the addition of poly-T tails (homopolymers of deoxythymidine) using the enzyme terminal deoxynucleotidyl transferase. A commercial kit (ENZO Biochem, New York) was used for this reaction. This reaction was terminated and the probe denatured by incubating at 98° C. for 10 minutes. The unlabelled probes, those with and without incorporated thionucleotides, were then placed directly on ice to prevent reannealing and a low salt buffer (10 mM NaCl, 1 mM Tris Cl, pH 7.5, 0.1 mM EDTA where Tris was tris (hydroxymethyl) aminomethane) added to adjust the final probe concentration to 10 ng/μl.

Thereafter, the hybridization buffer bathing two of the strips was brought to 20 mM $Cu^{2+}$ by the addition of 20 μl of 1M $CuCl_2$. The other two strips were bathed in the same buffer but without the addition of $Cu^{2+}$. Of the two strips bathed in the buffer with $Cu^{2+}$, one received 500 ng of control probe and the other received 500 ng of thionucleotide-containing probe. Similarly, of the two strips bathed in the buffer without $Cu^{2+}$, one received 500 ng of control probe and the other received 500 ng of thionucleotide-containing probe. Each strip was heat-sealed with its buffer in a bag and incubated at 65° C. for 29 hours. Following hybridization, the strips were washed twice at room temperature for 5 minutes in 0.3M NaCl, 30 mM Na citrate, 0.1 percent SDS, twice at 65° C. for 30 minutes each wash in 0.3M NaCl, 30 mM Na citrate, 0.1 percent SDS, and once for 10 minutes at 42° C. in 15 mM NaCl, 1.5 mM Na citrate, 0.1 percent SDS.

Following hybridizing and washing, a non-radiometric labelling molecule was added by annealing a polymer of biotinylated adenosine (Bio-Bridge A, ENZO Biochem, New York) to the poly-T tail of any bound (annealed) probe molecules, both control and thionucleotide-containing. The annealing procedure recommended by ENZO Biochem was followed precisely, including the subsequent washes. The membranes were then incubated overnight at 65° C. in a blocking buffer containing 3 percent bovine serum albumin in 100 mM Tris Cl pH 7.5, 150 mM NaCl. The biotinylated DNA was detected by binding strepavidin to the biotinylated polyA and then binding biotin conjugated to alkaline phosphatase to the strepavidin (the commercial DNA Detection System sold by Bethesda Research Labs was used). The alkaline phosphatase was then activated in the presence of the dyes 5-bromo-4-chloro-3-indolyl phosphate and nitroblue tetrazolium to produce a blue precipitate. The membranes are shown photographed in FIG. 1.

In FIG. 1, Column "A" represents the hybridization reaction involving the control probe and a buffer free of $Cu^{2+}$. Column "B" represents the same reaction except for the presence of $Cu^{2+}$ in the buffer. Column "C" represents the reaction in which the thionucleotide-containing probe was hybridized to the target DNA in the presence of $Cu^{2+}$. Column "D" represents the same reaction as column "C" except for the absence of $Cu^{2+}$ in the buffer. As columns C and D illustrate, the addition of 20 mM $Cu^{2+}$ produced an increase in both the intensity of the color development and the sensitivity of the hybridization reaction with 25 pg being darkly visualized and 5 pg lightly visualized with thionucleotide probes in the presence of $Cu^{2+}$ compared to 125 pg in the absence of $Cu^{2+}$. Notably, even without $Cu^{2+}$, the thionucleotide probes of column D showed increased binding as compared to the control probes of columns A and B.

Similar experiments were performed on five separate occasions, with similar results. Table V presents a summary of these experiments. In the absence of $Cu^{2+}$, a 5-8 fold increase in sensitivity was generally observed with thionucleotide-containing probes. This improvement increased to 10-25 fold in the presence of $Cu^{2+}$. By way of note, the detection limit was determined by visual inspection of the colorimetric signal produced by DNA "dots" of decreasing concentration in the following series: 1 ng, 500 pg, 250 pg, 125 pg, 62.5 pg, 25 pg, 5 pg, 0 pg (500 pg of non-homologous salmon sperm DNA as a negative control). Any dot visible by eye over the negative control was scored. Target DNA was immobilized on the charged nylon membrane GeneScreen Plus ™ according to the protocol supplied by New England Nuclear.

TABLE V

Summary of Detection Limits Obtained With T-tailed DNA Probes Constructed With or Without Thionucleotides

| Experiment | Control Probes | Probes w/Thiol | Ratio (Control/αS) |
|---|---|---|---|
| No Cation Additions | | | |
| KR 1057 | 625 | 125 | 5 |
| KR 1077a | 1000 | 125 | 8 |
| KR 1080a | 1000 | 125 | 8 |
| Addition of 10-20 mM $Cu^{2+}$ | | | |
| KR 1070 | 125 | 5 | 25 |
| KR 1072 | 250 | 25 | 10 |
| KR 1077b | 250 | 25 | 10 |
| KR 1080b | 125 | 5 | 25 |
| KR 1082[1] | 500 | 25 | 20 |

[1]Hybridization reactions were conducted for 16-20 hours, except for KR 1082, which represented a 4 hour hybridization.

EXAMPLE 8

Results Obtained with 4 Hour Hybridization in the Presence of $Cu^{2+}$

Figure 2:
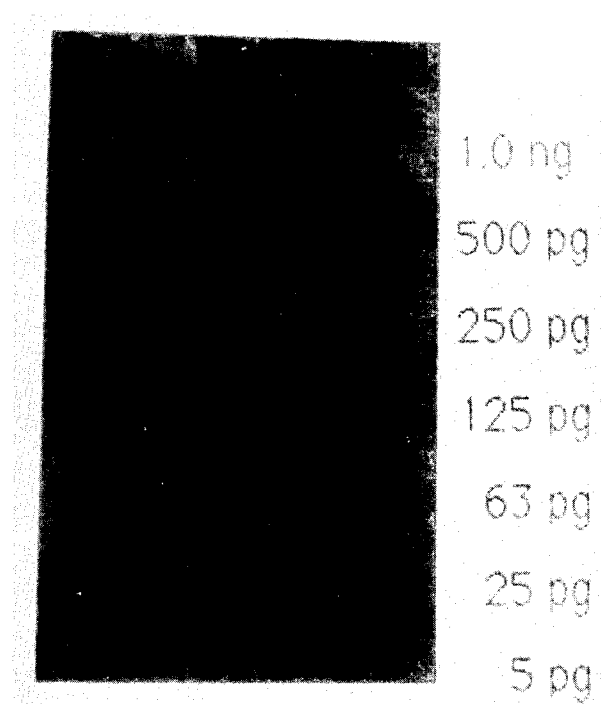

In this example, the experiments of columns B and C (FIG. 1) of Example 7 were repeated with two exceptions: the hybridization incubation was shortened to 4 hours and the blocking incubation in bovine serum albumin was shortened to 1 hour. This permitted completion of the hybridization and detection procedures in the equivalent of one working day. The resulting membranes are shown photographed in FIG. 2. Shortening the hybridization reaction in which $Cu^{2+}$ was present decreased the sensitivity of the procedure to 500 pg for control probes (normally 125-250 pg) and 25 pg for thionucleotide-containing probes.

EXAMPLE 9

Effect of Different Cations on the Hybridization Sensitivity of Radiometric Probes Bacteriophage lambda DNA was obtained from a commercial source (New England BioLabs, Cambridge, Mass.) at a concentration of 0.5 μg/μl. The double-stranded DNA was denatured in 0.5N NaOH for 10 minutes at room temperature, then placed on ice and neutralized by dilution in a neutralizing buffer (1M Tris Cl, pH 7.5). Dilutions of denatured DNA were applied to nylon membranes (GeneScrene Plus, NEN Research Products) using a Hybri-Dot (TM) manifold (Bethesda Research Labs) in a series of decreasing concentrations from 250 pg/dot to 1 pg dot. One row contained 1 ng/dot herring sperm DNA as a control for non-specific binding of the probes to non-homologous DNA. The membranes were dried at 80° C. for 1-2 hours. Each membrane was divided into six strips, each containing two columns with eight rows of DNA. Two membranes, totalling 12 strips, were used in this example. The strips were pre-hybridized in 10 ml of 0.75M NaCl, 75 mM Na citrate, 1 percent SDS for 7 hours at 65° C.

Experimental probes of bacteriophage lambda DNA were dually labelled by nick translation in the presence of α-[$^{32}$P]-deoxycytidine triphosphate and α-[$^{35}$S]-deoxyadenosine-1-O thiotriphosphate using the method of Rigby et al. (1977). In this experiment, [$^{35}$S]-dATP was used because it was available as 98 percent pure Sp diastereomer. The nearly 50 percent levels of Rp diastereomer present in commercially available $^{32}$S-dATP significantly inhibit the nick translation reaction. Control probes were labelled with α-[$^{32}$P]-deoxycytidine triphosphate alone. Unincorporated radionucleotides were removed by precipitation in cold ethanol. Both the experimental and control probes were then resuspended in a low salt buffer (10 mM NaCl, 1 mM Tris HCl pH 7.5, 0.1 mM EDTA) at a final concentration of 10 ng/μl. They were denatured by incubating at 98°-100° C. for 10 minutes and then placed directly on ice to prevent reannealing. The specific activity of the probes was 1.2 to 1.6×10$^8$ dpm/μg at an energy window between 170 and 1700 KeV.

Each of twelve strips prepared as described above (six with $^{35}$S and six without) was placed in an individual bag to which 1 ml of a selected experimental or control hybridization buffer was added. The hybridization buffer comprised 0.75M NaCl 75 mM Na citrate 1 percent SDS and either 20 mM $CuCl_2$, 20 mM $FeCl_3$, 20 mM $CoCl_2$, 20 mM $CdCl_2$, 20 mM $ZnCl_2$ or in the case of the control buffer no additional cations. The hybridization buffer also contained 33-40 ng/ml of one of the radiolabelled DNA probes, either control or thionucleotide-containing. The strips were incubated at 65° C. for 21.5 hours, then washed in 0.3M NaCl, 30 mM Na citrate 0.1 percent SDS, twice at room temperature for 5 minutes each wash, then twice at 65° C. for 30 minutes each wash. The membranes were then washed for 1 hour in 0.03M NaCl, 3 mM Na citrate, 0.1 percent SDS at 50° C.

Autoradiography was performed using Kodak X-AR film with DuPont Quanta II (TM) intensifying screens at −70° C. for 20 hours. The autoradiograph was used to identify the hybridized dots on the membranes, and these were excised and counted in a Packard liquid scintillation counter. The mass of probe DNA bound was calculated from the specific activity of the probe and the counts bound to the membranes in a conventional manner, and used to construct Table VI. The data were corrected for the non-specific binding observed between the probe DNA and the non-homologous herring sperm DNA. The presence of either $Cu^{2+}$, $Fe^{3+}$, or $Co^{2+}$ in the hybridization buffer produced a significant increase in the binding of thionucleotide probes as compared to the control reaction (column C) in which the thionucleotide probe was hybridized to the denatured target DNA in a buffer lacking additional cations. The presence of $Zn^{2+}$ in the buffer produced a slight decrease in specific thionucleotide probe binding under these conditions. The presence of $Cd^{2+}$ appeared to reduce thionucleotide probe binding significantly.

ate group as compared to the oxyanion moiety. Stated differently, the attraction between the cation and thiol groups must be sufficiently strong to promote a specific dative bond *not* observed in reactions between that cation and the oxyanion portion of conventional phosphodiester linkages. Ideally, the particular cation should interact with the thiol moiety with enough strength to maintain two thionucleotide-containing molecules in close proximity throughout the harsh conditions of the wash procedure, while displaying a high degree of specificity for the thiol moiety so as to avoid non-specific attachments between thionucleotide-containing probe molecules and the oxyanions present in non-complementary regions of DNA, or between probe molecules and random negatively-charged regions on the membrane.

The foregoing data establishes that certain cations, namely $Fe^{3+}$, $Co^{2+}$ and $Cu^{2+}$, promote increased binding in hybridization reactions involving thionucleotide-containing probes. In view of the foregoing theoretical analysis, common properties typically exhibited by cations in the same family, and high affinities of group VIII and IB cations for sulfur atoms, it is expected that the other cations in the $Fe^{3+}$, $Co^{2+}$ and $Cu^{2+}$ families, as

TABLE VI

| | Cation Effect on Thionucleotide Probe Binding - in pg. Probe DNA Bound to Target DNA | | | | | | | | | | | |
|---|---|---|---|---|---|---|---|---|---|---|---|---|
| Target DNA | Control | Thiol Control | $Cu^{2+}$ | Thiol $Cu^{2+}$ | $Fe^{3+}$ | Thiol $Fe^{3+}$ | $Cd^{2+}$ | Thiol $Cd^{2+}$ | $Co^{2+}$ | Thiol $Co^{2+}$ | $Zn^{2+}$ | Thiol $Zn^{2+}$ |
| 250 pg | 2.18 | 12.5 | 3.87 | 27.4 | 4.15 | 34.5 | 2.2 | 1.2 | 0.98 | 43.2 | 2.67 | 12.1 |
| 175 pg | 2.23 | 15.9 | 3.23 | 30.2 | 4.2 | 32.9 | 1.25 | 3.1 | 1.29 | 29.8 | 4.3 | 9 |
| 35 pg | 0.88 | 8.7 | 3.88 | 20.4 | 3.13 | 31.8 | | 2.5 | 0.83 | 34.4 | 3.54 | 5.7 |
| 6 pg | 0 | 7.6 | 0.82 | 12.9 | 2.12 | 15.4 | 0.77 | | 1.46 | 25.8 | 1.22 | 7 |
| Sum | 5.29 | 44.7 | 11.8 | 90.9 | 13.6 | 114.6 | 4.22 | 6.8 | 4.56 | 133.2 | 11.73 | 33.8 |
| Ratio (Cation/No Cation) | | 8.45x | | 7.70x | | 8.43x | | 1.61x | | 29.21x | | 2.88x |

Sum = sum of all probe bound to membrane
"Ratio" is the ratio of binding observed with thionucleotide probes to binding observed with control probes, under the same hybridization conditions, i.e., with the same cations present

EXAMPLE 10

The experiment of Example 9 was repeated under the same conditions except where noted. The hybridization buffers contained either 20 mM $CuCl_2$, 20 mM $AgCl_2$, 20 mM $OsCl_3$, 20 mM $ZnCl_2$ or, in the case of the control buffer, no additional cations. The mass of probe DNA probe bound for 250 pg of denatured target DNA is summarized in Table VII.

well as those cations in the $Ni^{2+}$ family, can also be used to promote increased binding in such reactions.

Based upon present data, the following observations can be made to predict which cations are most likely to promote increased binding of thionucleotide-containing probes:

(1) the cation should be multivalent to permit simultaneous interaction with more than one thionucleotide;
(2) the cation should have a higher affinity for thiol

TABLE VII

| | Cation Effect on Thionucleotide Probe Binding - in pg. Probe DNA Bound to Target DNA | | | | | | | | | |
|---|---|---|---|---|---|---|---|---|---|---|
| Target DNA | Control ($^{32}$P/No Cations) | Thiol Control (No Cations) | $Cu^{2+}$ | Thiol $Cu^{2+}$ | $Ag^{2+}$ | Thiol $Ag^{2+}$ | $Os^{3+}$ | Thiol $Os^{3+}$ | $Zn^{2+}$ | Thiol $Zn^{2+}$ |
| 250 pg | 8.0 | 61.0 | 9.8 | 83 | 16 | 49 | 14 | 103 | 3.75 | 74 |
| Ratio | | 7.6x | | 8.5x | | 3.1x | | 7.4x | | 20x |

"Ratio" is the ratio of binding observed with thionucleotide probes to binding observed with control probes, under the same hybridization conditions, i.e., with the same cations present It is believed that the present invention results in increased binding of detectable molecules because of crosslinking reactions which occur between probe molecules containing phosphorothioate groups. Dative bonds (or coordination complexes) between phosphorothioate groups and multivalent cations are probably responsible for the crosslinking. The presence of selected divalent or multivalent cations appears to promote the formation of coordination complexes. It is believed that a particular cation's ability to promote crosslinking is a function of that cation's relative affinity or specificity for the thiol moiety of the phosphorothiogroups than for oxyanions;
(3) the cation should have a fairly substantial redox potential, more electronegative than +0.4; and
(4) the cation should be present in the buffer at appropriate concentrations.

Regarding cation concentration, an insufficient cation concentration will fall short of optimizing increased binding. An excess concentration may cause aggregation of nucleic acid macromolecules, thereby causing such macromolecules to precipitate out of solution. This would decrease the availability of probe molecules in solution for annealing with target molecules and could result in a large increase in non-specific binding as well. Optimal cation concentrations are believed to range from equimolar cation and thiol groups to a 10-fold excess of cations. A cation ($Cu^{2+}$) concentration greater than 100-fold molar excess consistently decreased specific binding to the target.

It will be appreciated that the thionucleotide-containing probe need not be labelled prior to the hybridization step. An unlabelled thionucleotide-containing probe could be annealed to the complementary DNA target molecule and thereafter labelled, as in the case of Example 7, wherein biotinylated adenosine was annealed to the poly-T tail of the probe.

Alternatively, following hybridization, a labelling or reporter molecule having both a detectable label and incorporated thionucleotides (making it capable of interacting specifically with the thionucleotide-containing probe portion of the annealed nucleotide sequence) could be annealed to the probe portion of the annealed nucleotide sequence. Like the annealing of the probe molecule to the target, the annealing of the labelling molecule to the probe portion of the annealed nucleotide sequence could be done in the presence of millimolar amounts of one or more selected cations in the manner described above. The same phosphorothioate coordination complexes which serve to crosslink probe and target molecules can also serve to crosslink the labelling molecules to the probe portion of the annealed nucleotide sequence, thereby increasing the mass of labelling molecules otherwise bound and amplifying the signal used to detect the presence of the nucleotide sequence of interest. This modification is advantageous in that the labelling molecule with its incorporated phosphorothioate group can be constructed synthetically and need not be complementary to the target DNA sequence of interest, thereby reducing the amount of probe molecules and attendant expense required for the hybridization reaction.

It will be apparent from the foregoing description that cations having a high specific affinity for the thiol moiety of phosphorothioate-containing probes could be used to convey a detectable label directly to the probe molecule. Cations could themselves be radionuclides, or they could be conjugated to detectable labels such as dye molecules or dye-activating enzymes. Cations complexed to phosphorothioate groups may themselves participate in additional chemical reactions (notable oxidation-reduction reactions) which could form the basis of a chemical detection system. Additionally, the affinity of these cations for phosphorothioate groups could be exploited for the isolation and/or purification of desired sequences. Target sequences could be annealed to thionucleotide-containing probes, and the complexes allowed to react with appropriate cations immobilized on an affinity column or other substrate.

Although the foregoing invention has been described in some detail by way of illustration and example for purposes of clarity of understanding, it is obvious that certain changes and modifications may be practiced within the scope of the appended claims.

We claim:

1. A method for detecting the presence of specific nucleic acid base sequences in a sample suspected of containing said sequences in single-stranded form comprising:
providing nucleic acid probe molecules which in single-stranded form are capable of binding specifically to said suspected nucleic acid base sequences and contain at least one thionucleotide;
converting any double-stranded probe molecules to single-stranded form;
annealing said single-stranded, thionucleotide-containing probe molecules to said suspected nucleic acid base sequences in the presence of a concentration of multivalent cations capable of promoting the formation of ionic interactions between phosphorothioate groups of said probe molecules;
subsequent to said annealing, detecting the presence of any said probe molecules annealed to said suspected nucleic acid base sequences; and
prior to said detecting, providing said probe molecules with a detectable label to provide a means for later detecting the presence of any said probe molecules annealed to said suspected nucleic acid base sequences.

2. A method for detecting the presence of specific nucleic acid base sequences in a sample suspected of containing said sequences in single-stranded form comprising:
providing nucleic acid probe molecules which in single-stranded form are capable of binding specifically to said suspected nucleic acid base sequences and contain at least one thionucleotide;
converting any double-stranded probe molecules to single-stranded form;
annealing said single-stranded, thionucleotide-containing probe molecules to said suspected nucleic acid base sequences in the presence of a concentration of multivalent cations selected from the group consisting of those transition metals in groups VIII, IB and IIB of the periodic table;
subsequent to said annealing, detecting the presence of any said probe molecules annealed to said suspected nucleic acid base sequences; and
prior to said detecting, providing said probe molecules with a detectable label to provide a means for later detecting the presence of any said probe molecules annealed to said suspected nucleic acid base sequences.

3. The method of claim 2 wherein said cation is selected from the group consisting of those group VIII and IB transition metals having a greater affinity for thiol groups than for oxyanions and a redox potential more electronegative than +0.4.

4. The method of claim 2 wherein said cations are selected from the group consisting of those transition metals in the iron and copper families.

5. The method of claim 2 wherein said cations are selected from the group consisting of $Cu^{2+}$ and $Fe^{3+}$.

6. The method of claim 3 wherein said cations are $Cu^{2+}$.

7. The method of claims 2, 3, 4, 5, or 6 wherein said cation is present in an amount ranging from about equimolar cation and thiol groups to about a 10-fold molar excess of cations to thiol groups.

8. The method of claims 2, 3 or 4 wherein said annealing occurs in the absence of EDTA.

9. The method of claims 2, 4 or 5 wherein said probe molecules are provided with said detectable label prior to said annealing.

10. The method of claims 2, 4 or 5 wherein said probe molecules are provided with said detectable label after said annealing.

11. The method of claim 2 wherein said detectable label is a chemical modification.

12. The method of claim 11 wherein said single-stranded thionucleotide-containing probe molecules are provided with poly T-tails and said detectable label is attached to a polymer of adenosine which is annealed to said poly T-tails.

13. The method of claim 12 wherein said detectable label is biotinylated adenosine.

14. The method of claims 2, 4 or 5 wherein racemically pure Sp thionucleotides are used to construct said thionucleotide-containing probe molecules.

15. A method for detecting the presence of specific nucleic acid base sequences in a sample suspected of containing said sequences in single-stranded form comprising:

providing nucleic acid probe molecules which in single-stranded form are capable of binding specifically to said suspected nucleic acid base sequences and contain at least one thionucleotide;

providing said probe molecules with a detectable label;

converting any double-stranded probe molecules to single-stranded form;

thereafter annealing said labelled, single-stranded thionucleotide-containing probe molecules to said suspected nucleic acid base sequences in the presence of a concentration of multivalent cations selected from the group consisting of those transition metals in groups VIII and IB of the periodic table;

thereafter detecting the presence of any said labelled probe molecules annealed to said suspected nucleic acid base sequences.

16. The method of claim 15 wherein racemically pure Sp thionucleotides are used to construct said thionucleotide-containing probe molecules.

17. The method of claim 15 wherein said detectable label is a radionuclide.

18. The method of claim 15 wherein said detectable label is a chemical modification.

19. A method for detecting the presence of specific nucleic acid base sequences in a sample suspected of containing said sequences in single-stranded form comprising:

providing nucleic acid probe molecules which in single-stranded form are capable of binding specifically to said suspected nucleic acid base sequences and contain at least one thionucleotide;

converting any double-stranded probe molecules to single-stranded form;

annealing said single-stranded, thionucleotide-containing probe molecules to said suspected nucleic acid base sequences in the presence of a concentration of multivalent cations selected from the group consisting of those transition metals in groups VIII and IB of the periodic table;

thereafter providing said probe molecules with a detectable label; and detecting the presence of any said labelled probe molecules annealed to said suspected nucleic acid base sequences.

20. The method of claim 19 wherein racemically pure Sp thionucleotides are used to construct said thionucleotide-containing probe molecules.

21. The method of claim 19 wherein said detectable label is a chemical modification.

22. The method of claim 19 wherein said single-stranded probe molecules are provided with poly T-tails and said detectable label is attached to a polymer of adenosine which is annealed to said poly T-tails.

23. The method of claim 19 wherein said detectable label is added to said thionucleotide-containing probe molecules by means of an ionic interaction between phosphorothioates and cations.

24. The method of claim 19 wherein said detectable label is a radionuclide.

25. The method of claim 19 wherein said detectable label includes labelling molecules each containing thionucleotides capable of interacting specifically with the thionucleotides of said probe molecules.

26. The method of claim 19 wherein following annealing said probe molecules are contacted with non-complementary thionucleotide-containing molecules in the presence of a cation forming ionic interaction, said non-complementary molecules containing a detectable label.

27. A hybridization probe for detecting the presence of specific nucleic acid base sequences in a sample suspected of containing said sequences comprising:

labelled single-stranded nucleic acid probe molecules having essentially complementary base sequences to defined regions in said suspected nucleic acid base sequences;

a detectable label attached to said probe molecules; and one or more phosphorothioate groups attached to said probe molecules which are capable of forming crosslinking ionic bonds with each other to bond together multiple labelled probe molecules, said phosphorothioate groups being non-radioactive.

* * * * *

UNITED STATES PATENT AND TRADEMARK OFFICE
CERTIFICATE OF CORRECTION

PATENT NO. : 4,908,307
DATED : March 13, 1990
INVENTOR(S) : Karin D. Rodland, Peter J. Russell It is certified that error appears in the above-identified patent and that said Letters Patent is hereby corrected as shown below:

Column 7, line 56, "ug" should be --µg--.

Column 12, line 51, "αthio" should be --α thio--.
Column 12, line 64, "used" should be --α-[$^{35}$S] used--.

Column 14, line 10, "100-500 µg" should be --100-500 ng--.

Signed and Sealed this

Seventh Day of April, 1992

Attest:

HARRY F. MANBECK, JR.

*Attesting Officer*     *Commissioner of Patents and Trademarks*